United States Patent [19]

Martin et al.

[11] Patent Number: 5,583,248

[45] Date of Patent: Dec. 10, 1996

[54] AMINO ACID DERIVATIVES HAVING ANTIVIRAL ACTIVITY

[75] Inventors: Joseph A. Martin, Harpenden; Gareth J. Thomas, Welwyn, both of England

[73] Assignee: Hoffmann-La Roche Inc., Nutley, N.J.

[21] Appl. No.: 417,315

[22] Filed: Apr. 5, 1995

Related U.S. Application Data

[62] Division of Ser. No. 871,880, Apr. 21, 1992, Pat. No. 5,430,041.

[30] Foreign Application Priority Data

May 10, 1991 [GB] United Kingdom .................... 9110170
Feb. 13, 1992 [GB] United Kingdom .................... 9203014

[51] Int. Cl.$^6$ ..................... C07C 233/58; C07C 271/20
[52] U.S. Cl. ................. 560/27; 558/393; 560/39; 560/40; 560/41; 560/115; 560/122; 560/125; 564/153; 564/152; 564/154; 564/155; 564/158
[58] Field of Search .................... 558/393; 560/27, 560/39, 40, 41, 115, 122, 125; 564/152, 153, 154, 155, 158

[56] References Cited

FOREIGN PATENT DOCUMENTS

| | | |
|---|---|---|
| 0274901 | 7/1988 | European Pat. Off. |
| 346847 | 12/1989 | European Pat. Off. |
| 038611 | 9/1990 | European Pat. Off. |
| 432695 | 6/1991 | European Pat. Off. |

OTHER PUBLICATIONS

D. H. Rich, et. al. Journal of Medicinal Chemistry, vol. 34, No. 3 Mar., 1991, pp. 1222–1225.

Primary Examiner—Richard L. Raymond
Attorney, Agent, or Firm—George M. Gould; William H. Epstein; Bruce A. Pokras

[57] ABSTRACT

Compounds of the formula:

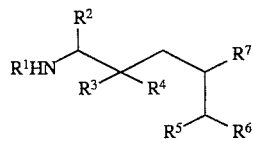

wherein $R^1$ is alkoxycarbonyl, aralkoxycarbonyl, alkanoyl, aralkanoyl, heterocyclylcarbonyl or a group of the formula:

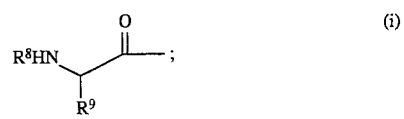

$R^2$ is alkyl, cycloalkylalkyl or aralkyl; $R^3$ is hydrogen and $R^4$ is hydroxy or $R^3$ and $R^4$ together are oxo; $R^5$ is alkoxycarbonyl or alkylcarbamoyl; $R^6$ and $R^7$ together are trimethylene or tetramethylene optionally substituted by alkyl or on adjacent carbon atoms by tetramethylene; $R^8$ is alkoxycarbonyl, aralkoxycarbonyl, alkanoyl, aroyl, aralkanoyl or heteroeyelylearbonyl; and $R^9$ is alkyl, cycloalkyl, cycloalkylalkyl, aralkyl, cyanoalkyl, carbamoyl-alkyl, alkylthioalkyl, alkoxyalkyl or alkoxycarbonylalkyl:

and pharmaceutically acceptable acid addition salts of those compounds of formula I which are basic, inhibit aspartyl proteases of viral origin and can be used in the form of medicaments for the prophylaxis or treatment of viral infections. They can be manufactured according to generally known methods.

20 Claims, No Drawings

AMINO ACID DERIVATIVES HAVING ANTIVIRAL ACTIVITY

This is a division of application Ser. No. 07/871,880 filed Apr. 21 1992, now U.S. Pat. No. 5,430,041.

SUMMARY OF THE INVENTION

The present invention relates to amino acid derivatives. More particularly, it is concerned with amino acid derivatives of the formula:

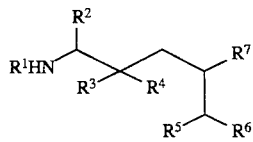

wherein $R^1$ is alkoxycarbonyl, aralkoxycarbonyl, alkanoyl, aralkanoyl, heterocyclylcarbonyl or a group of the formula:

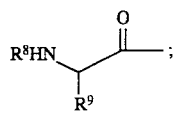

$R^2$ is alkyl, cycloalkylalkyl or aralkyl; $R^3$ is hydrogen and $R^4$ is hydroxy or $R^3$ and $R^4$ together are oxo; $R^5$ is alkoxycarbonyl or alkylcarbamoyl; $R^6$ and $R^7$ together are trimethylene or tretamethylene optionally substituted by alkyl or on adjacent carbon atoms by tetramethylene; $R^8$ is alkoxycarbonyl, aralkoxycarbonyl, alkanoyl, aroyl, aralkanoyl or heterocyclylcarbonyl; and $R^9$ is alkyl, cycloalkyl, cycloalkylalkyl, aralkyl, cyanoalkyl, carbamoylalkyl, alkylthioalkyl, alkoxyalkyl or alkoxycarbonylalkyl;
and pharmaceutically acceptable acid addition salts of those compounds of formula I which are basic.

The aforementioned compounds and salts of the invention are novel and possess valuable pharmacological properties. In particular, they inhibit aspartyl proteases of viral origin and can be used in the prophylaxis and treatment of viral infections, particularly of infections caused by HIV and other retroid viruses.

Objects of the present invention are the compounds of the invention and the aforementioned salts per se and the use of the compounds of the invention as therapeutically active substances, a process for the manufacture of said compounds and salts, intermediates used in said process, medicaments containing said compounds and salts, the use of said compounds and salts in the prevention or control of illnesses, especially in the prophylaxis or treatment of vital infections, and the use of said compounds and salts for the manufacture of medicaments for the prophylaxis or treatment of vital infections.

DETAILED DESCRIPTION OF THE INVENTION

As used in herein, the term "alkyl", alone or in combination, means a straight-chain or branched-chain alkyl group containing a maximum of 8, preferably a maximum of 4, carbon atoms such as methyl, ethyl, n-propyl, isopropyl, n-butyl, isobutyl, sec.butyl, tert.butyl, n-pentyl, n-hexyl and the like.

The term "alkoxy", alone or in combination, means an alkyl ether group in which the term "alkyl" has the significance given earlier, such as methoxy, ethoxy, n-propoxy, isopropoxy, n-butoxy, isobutoxy, sec.butoxy, tert.butoxy and the like.

The term "cycloalkyl", alone or in combination, means a cycloalkyl group containing 3–8, preferably 3–6, carbon atoms such as cyclopropyl, cyclobutyl, cyclopentyl, cyclohexyl and the like.

The term "aralkyl" means an alkyl group as defined earlier in which one hydrogen atom is replaced by an aryl group, i.e., a phenyl or naphthyl group which optionally carries one or more substituents selected from alkyl, alkoxy, halogen, trifluoromethyl, hydroxy, nitro, amine and the like. Examples of aralkyl groups are benzyl, 4-chlorobenzyl, 4-methoxybenzyl, 2-phenylethyl, 2-naphthylethyl and the like. The term "aralkyloxycarbonyl" means a group of the formula aralkyl-O—C(O)— in which the term "aralkyl" has the significance given earlier.

The term "alkanoyl" means an acyl group derived from an alkanecarboxylic acid such as acetyl, propionyl, butyryl, valeryl, 4-methylvaleryl and the like.

The term "aroyl" means a benzoyl or naphthoyl group which optionally carries one or more substituents selected from alkyl, alkoxy, halogen, trifluoromethyl, hydroxy, nitre, amine and the like, such as benzoyl, p-chlorobenzoyl, 3,5-dichlorobenzoyl, 1-naphthoyl and the like.

The term "aralkanoyl" means an acyl group derived from an aryl-substituted alkanecarboxylic acid such as phenylacetyl, 3-phenylpropionyl (hydrocinnamoyl), 4-phenylbutyryl, (2-naphthyl)acetyl, 4-chloro-, 4-amino- or 4-methoxyhydrocinnamoyl and the like.

The term "heterocyclylcarbonyl" means a group of the formula —CO-Het in which Het is a saturated, partially unsaturated or aromatic monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo etc and/or on a secondary nitrogen atom (i.e. —NH—) by alkyl, aralkoxycarbonyl, alkanoyl, phenyl or phenylalkyl or on a tertiary nitrogen atom (i.e. =N—) by oxide and which is attached via a carbon atom. Examples of such Het groups are pyrrolidinyl, piperidinyl, morpholinyl, thiomorpholinyl, pyrrolyl, imidazolyl, pyrazolyl, pyridyl, pyrazinyl, pyrimidinyl, furyl, thienyl, triazolyl, oxazolyl, thiazolyl, indolyl, quinolyl, isoquinolyl, tetrahydroquinolyl, 1,2,3,4-tetrahydroisoquinolyl, quinoxalinyl, β-carbolinyl and the like.

The term "halogen" means fluorine, chlorine, bromine and iodine.

The pharmaceutically acceptable acid addition salts are formed between basic compounds of the invention and inorganic acids, e.g., hydrohalic acids such as hydrochloric acid and hydrobromic acid, sulphuric acid, nitric acid, phosphoric acid, etc., or organic acids, e.g., acetic acid, citric acid, maleic acid, fumaric acid, tartaric acid, methanesulphonic acid, p-toluenesulphonic acid, etc.

The compounds of the invention contain at least three asymmetric carbon atoms and are therefore present in the form of optically pure diastereoisomers, mixtures of diastereoisomers, diastereoisomeric racemates or mixtures of diastereoisomeric racemates. The present invention includes all of these forms within its scope.

The invention comprises compounds of the formula:

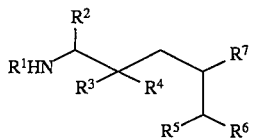

wherein $R^1$ is alkoxycarbonyl, aralkoxycarbonyl, alkanoyl, aralkanoyl, heterocyclylcarbonyl or a group of the formula:

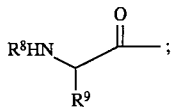

$R^2$ is alkyl, cycloalkylalkyl or aralkyl; $R^3$ is hydrogen and $R^4$ is hydroxy or $R^3$ and $R^4$ together are oxo; $R^5$ is alkoxycarbonyl or alkylcarbamoyl; $R^6$ and $R^7$ together are trimethylene or tetramethylene optionally substituted by alkyl or on adjacent carbon atoms by tetramethylene; $R^8$ is alkoxycarbonyl, aralkoxycarbonyl, alkanoyl, aroyl, aralkanoyl or heterocyclylcarbonyl; and $R^9$ is alkyl, cycloalkyl, cycloalkylalkyl, aralkyl, cyanoalkyl, carbamoylalkyl, alkylthioalkyl, alkoxyalkyl or alkoxycarbonylalkyl,
and pharmaceutically acceptable acid addition salts of those compounds of formula I which are basic.

The invention also comprises compounds of formula I wherein $R^1$ is a group of formula (i) in which $R^8$ is alkoxycarbonyl, aralkoxycarbonyl, alkanoyl, aralkanoyl or heterocyclylcarbonyl, and all other groups are as above.

The invention also comprises compounds of formula I wherein $R^1$ is alkoxycarbonyl, $R^2$ is aralkyl, $R^3$ is hydrogen and $R^4$ is hydroxy or $R^3$ and $R^4$ together are oxo; $R^5$ is alkoxycarbonyl or alkylcarbamoyl; $R^6$ and $R^7$ together are trimethylene or tetramethylene optionally substituted by alkyl or on adjacent carbon atoms by tetramethylene; and pharmaceutically acceptable acid addition salts of those compounds which are basic. Of these compounds, those wherein $R^1$ is tert-butoxycarbonyl, $R^2$ is benzyl, $R^3$ is hydrogen, $R^4$ is hydroxy, $R^5$ is methoxycarbonyl or tert-butylcarbamoyl, and $R^6$ and $R^7$ together are unsubstituted tetramethylene are particularly preferred.

The invention also comprises compounds of formula I wherein $R^1$ is a group of formula (i) in which $R^8$ is aralkoxycarbonyl, aroyl or heterocyclylcarbonyl and $R^9$ is alkyl, aralkyl, cyanoalkyl, carbamoylalkyl, alkylthioalkyl or alkoxycarbonylalkyl; $R^2$ is aralkyl. $R^3$ is hydrogen and $R^4$ is hydroxy or $R^3$ and $R^4$ together are oxo; $R^5$ is alkoxycarbonyl or alkylcarbamoyl; $R^6$ and $R^7$ together are trimethylene or tetramethylene optionally substituted by alkyl or on adjacent carbon atoms by tetramethylene; and pharmaceutically acceptable acid addition salts of those compounds which are basic. Of these compounds, those wherein $R^8$ is benzyloxycarbonyl, 3,5-dichlorobenzoyl or 2-quinolylcarbonyl and $R^9$ is isopropyl, tert.butyl, benzyl, cyanomethyl, carbamoylmethyl, methylthiomethyl or methoxycarbonylmethyl, $R^2$ is benzyl, $R^3$ is hydrogen, $R^4$ is hydroxy, $R^5$ is methoxycarbonyl or tert-butylcarbamoyl, and $R^6$ and $R^7$ together are unsubstituted tetramethylene are preferred. Also preferred among these compounds are those wherein $R^3$ and $R^4$ together are oxo.

One especially preferred compound of the invention is:
2(S)-[3(S)-[[N-(2-quinolylcarbonyl)-L-asparaginyl]amino]-2(R)-hydroxy-4-phenylbutyl]-N-tert.butyl-1(R)-cyclohexanecarboxamide.

Other especially preferred compounds of the invention are:

2(S)-[3(S)-[[N-(benzyloxycarbonyl)-3-cyano-L-alanyl]amino ]-2(R)-hydroxy-4-phenylbutyl]-N-tert.butyl-1(R)-cyclohexanecarboxamide, 2(S)-[3(S)-[[N-(benzyloxycarbonyl)-L-valyl]amino]-2(R)-hydroxy-4-phenylbutyl]-N-tert.butyl-1(R)-cyclohexanecarboxamide, 2(S)-[3(S)-[[N-(benzyloxycarbonyl)-L-phenylalanyl]amino]-2(R)-hydroxy-4-phenylbutyl ]-N-tert.butyl-1(R)-cyclohexanecarboxamide, 2(S)-[3(S)-[[N-(2-quinolylcarbonyl)-L-valyl]amino]-2(R)-hydroxy-4-phenylbutyl]-N-tert.butyl-1(R)-cyclohexanecarboxamide, 2(S)-[3(S)-[[N-(benzyloxycarbonyl)-S-methyl-L-cysteinyl]amino]-2(R)-hydroxy-4-phenylbutyl]-N-tert.butyl-1(R)-cyclohexanecarboxamide, 2(S)-[3(S)-[[N-(benzyloxycarbonyl)-L-valyl]amino]-2-oxo-4-phenylbutyl]-N-tert.butyl-1(R)-cyclohexanecarboxamide, 2(S)-[3(S)-[[N-(benzyloxycarbonyl)-O-methyl-L-aspartyl]amino]-2(R)-hydroxy-4-phenylbutyl]-N-tert.butyl-1(R)-cyclohexanecarboxamide, 2(S)-[3(S)-[[N-(3,5-dichlorobenzoyl)-L-asparaginyl]amino]- 2(R)-hydroxy-4-phenylbutyl]-N-tert.butyl-1(R)-cyclohexanecarboxamide, 2(S)-[3(S)-[[N-(benzyloxycarbonyl)-3-methyl-L-valyl]amino]-2(R)-hydroxy-4-phenylbutyl]-N-tert.butyl-1(R)-cyclohexanecarboxamide, and methyl 2(S)-[3(S)-(tert.butoxyformamido)-2(R)-hydroxy-4-phenylbutyl]-1(R)-cyclohexanecarboxylate.

Examples of other interesting compounds of the invention are:

2(S)-[3(S)-[[N-(benzyloxycarbonyl)-L-asparaginyl]amino]-2(R)-hydroxy-4-phenylbutyl]-N-tert.butyl-1(R)-cyclohexananecarboxamide, 2(S)-[3(S)-(tert.butoxyformamido)-2(R)-hydroxy-4-phenylbutyl]-N-tert.butyl-1(R)-cyclohexanecarboxamide 2(R)-[3(S)-(tert.butoxyformamido)-2(R)-hydroxy-4-phenylbutyl]-N-tert.butyl-1(R)-cyclohexanecarboxamide, and 2(R)-[3(S)-[[N-(benzyloxycarbonyl)-L-asparaginyl]amino]-2(R)-hydroxy-4-phenylbutyl]-N-tert.butyl-1(R)-cyclohexanecarboxamide.

According to the process provided by the present invention, the compounds of the invention and the pharmaceutically acceptable acid addition salts of those compounds which are basic are manufactured by (a) for the manufacture of a compound of the invention in which $R^1$ is alkoxycarbonyl or aralkoxycarbonyl, $R^3$ is hydrogen and $R^4$ is hydroxy, treating a compound of the general formula

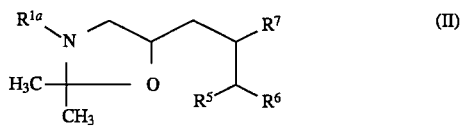

wherein $R^{1a}$ is alkoxycaxbonyl or aralkoxycarbonyl and $R^2$, $R^5$, $R^6$ and $R^7$ have the significance given earlier, with an acid, or (b) reacting a compound of the general formula

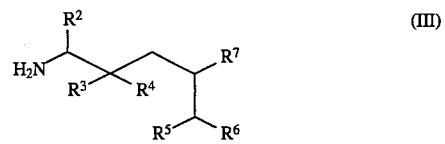

wherein $R^2$, $R^3$, $R^4$, $R^5$, $R^6$ and $R^7$ have the significance given earlier, with an acylating agent which introduces a group $R^1$ as defined earlier, or (c) for the manufacture of a compound of the invention in which $R^1$ is a group of formula (i), reacting a compound of the general formula

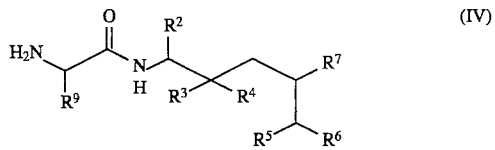

(IV)

wherein $R^2$, $R^3$, $R^4$, $R^5$, $R^6$, $R^7$ and $R^9$ have the significance given earlier, with an acylating agent which introduces a group $R^8$ as defined earlier, or (d) for the manufacture of a compound of the invention in which $R^3$ and $R^4$ together are oxo, oxidizing a compound of the invention in which $R^3$ is hydrogen and $R^4$ is hydroxy, and/or (e) if desired, separating a mixture of diastereoisomeric racemates into the diastereoisomeric racemates or optically pure diastereoisomers, and/or (f) if desired, separating a mixture of diastereoisomers into the optically pure diastereoisomers, and/or (g) if desired, converting a basic compound of the invention obtained into a pharmaceutically acceptable acid addition salt.

The treatment of a compound of formula II with an acid in accordance with embodiment (a) of the process yields a compound of the invention in which $R^1$ is alkoxycarbonyl or aralkoxycarbonyl, $R^3$ is hydrogen and $R^4$ is hydroxy. The type of acid which is used in this embodiment depends essentially on the nature of the substituent $R^{1a}$ present in the starting material of formula II. When $R^{1a}$ is alkoxycarbonyl, e.g., tert.butoxycarbonyl, the treatment is preferably carried out using a strong organic acid, especially an organic sulphonic acid such as an alkanesulphonic acid, e.g., methanesulphonic acid etc, or an aromatic sulphonic acid, e.g., benzenesulphonic acid, p-toluenesulphonic acid, mesitylenesulphonic acid etc, and in the presence of an organic solvent which is inert under the reaction conditions, e.g., an alkanol such as methanol, ethanol etc. A halogenated alkanecarboxylic acid, e.g., trifluoroacetic acid etc, can, however, be used in place of an organic sulphonic acid. When $R^{1a}$ is aralkoxycarbonyl, e.g., benzyloxycarbonyl, the treatment is preferably carried out using a solution of a hydrogen halide, e.g., hydrogen chloride, in an alkanol, e.g., methanol, and in the presence of an organic solvent which is inert under the-reaction conditions, e.g., a halogenated aliphatic hydrocarbon such as dichloromethane etc.

The reaction of a compound of formula III with an acylating agent in accordance with embodiment (b) of the process can be carried out in a manner known per se using as the acylating agent a corresponding acid or a reactive derivative thereof. Suitable reactive derivatives are the acid halides, e.g., acid chlorides, acid anhydrides, mixed anhydrides, activated esters etc. When the acylating agent is one which introduces a group of formula (i), the reaction is expediently carried out using the acid in the presence of a condensation agent, e.g., dicyclohexylcarbodiimide or benzotriazol-1-yloxy-tris(dimethylamino)phosphonium hexafluorophosphate, and in the presence of a base such as triethylamine, ethyldiisopropylamine and the like. The reaction is suitably carried out at a temperature between about 0° C. and about room temperature, preferably at room temperature.

The reaction of a compound of formula IV with an acylating agent in accordance with embodiment (c) of the process can be carried out in a manner known per se using as the acylating agent a corresponding acid or a reactive derivative thereof. Suitable reactive derivatives are the acid halides, e.g., acid chlorides, acid anhydrides, mixed anhydrides, activated esters etc. The reaction is suitably carried out at a temperature between about 0° C. and about room temperature, preferably at room temperature.

The oxidation in accordance with embodiment (d) of the process can be carried out in a manner known per se for the oxidation of secondary alcohols to ketones. Thus, for example, the oxidation can be carried out using pyridinium dichromate in dimethylformamide, pyridinium chlorochromate in dichloromethane, sulphur trioxide-pyridine complex in dimethyl sulphoxide, oxalyl chloride and triethylamine in dimethyl sulphoxide, dicyclohexylcarbodiimide and an organic acid such as dichloroacetic acid or trifluoroacetic acid in dimethyl sulphoxide.

The optional separations in accordance with embodiments (e) and (f) of the process can be carried out according to conventional methods, e.g., by column chromatography, thin-layer chromatography, high pressure liquid chromatography etc.

The conversion of a basic compound of the invention into a pharmaceutically acceptable salt in accordance with embodiment (g) of the process can be carried out by treatment in a conventional manner with an inorganic acid, e.g., a hydrohalic acid such as hydrochloric acid or hydrobromic acid, sulphuric acid, nitric acid, phosphoric acid etc, or with an organic acid, e.g., acetic acid, citric acid, maleic acid, fumaric acid, tartaric acid, methanesulphonic acid, p-toluenesulphonic acid etc.

The compounds of formula II which are used as starting materials in embodiment (a) of the process are novel and form a further object of the present invention. They can be prepared in accordance with the following Reaction Scheme in which $R^{1a}$, $R^2$, $R^6$ and $R^7$ have the significance given earlier.

Reaction Scheme

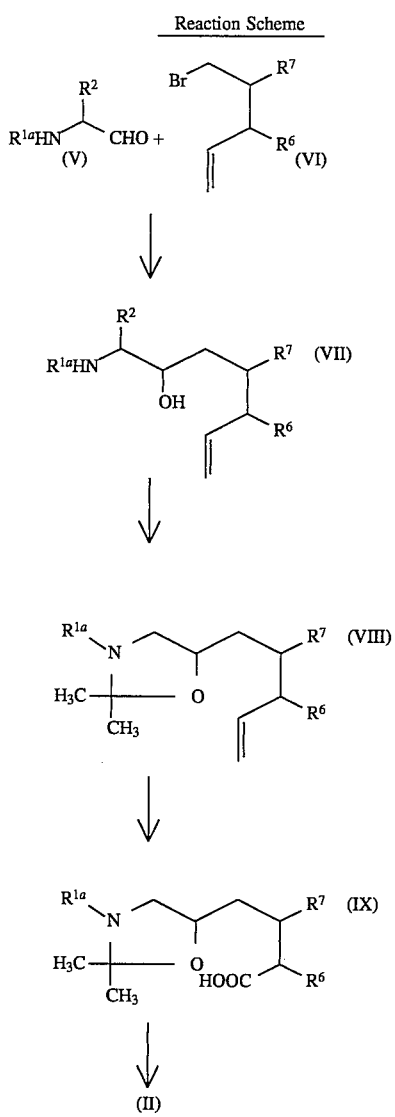

Having regard to the foregoing Reaction Scheme, in the first step a compound of formula V is reacted with a compound of formula VI to give a compound of formula VII. The reaction is carried out under the conventional conditions of a Grignard reaction; for example, in an organic solvent which is inert under the reaction conditions, such as an ether, e.g., diethyl ether, and at a temperature between about 0° C. and about 40° C., preferably at about room temperature.

In the next step, a compound of formula VII is converted into a compound of formula VIII by reaction with 2,2-dimethoxypropane in the presence of a strong organic acid, preferably an organic sulphonic acid such as p-toluenesulphonic acid. The reaction is conveniently carried out at about room temperature.

Subsequently, a compound of formula VIII is oxidized to a compound of formula IX. The oxidation is preferably carried out using an alkali metal permanganate such as potassium permanganate at about room temperature. Conveniently, the oxidation is carried out in a solvent system comprising a mixture of water, an alkanecarboxylic acid such as glacial acetic acid and an inert organic solvent which is not miscible therewith, e.g., an aromatic hydrocarbon such as benzene, toluene etc., and in the presence of a phase transfer catalyst.

Finally, a compound of formula IX is converted into a compound of formula II by esterification or amidation. The esterification or amidation be carried out by reacting a compound of formula IX with an appropriate alkanol or amine according to methods known per se.

The compounds of formulae V and VI, which are used for the preparation of the compounds of formula II, are known compounds or analogues of known compounds which can be prepared in a similar manner to the known compounds. Moreover, the Examples hereinafter contain detailed information relating to the preparation of certain compounds of formulae VI. The compounds of formulae VII, VIII and IX are, on the other hand, novel and are an object of the present invention.

The compounds of formula III which are used as starting materials in embodiment (b) of the process are novel and also form an object of the present invention. They can be prepared by cleaving off the alkoxycarbonyl or aralkoxycarbonyl group from a compound of the invention in which $R^1$ is an alkoxycarbonyl or aralkoxycarbonyl group. The cleavage can be carried out according to methods known per se. For example, when $R^1$ is an alkoxycarbonyl the cleavage can be carried out using a strong inorganic acid such as a hydrohalic acid or a strong organic acid, e.g., trifluoroacetic acid, conveniently at about 0° C. to about room temperature and when $R^1$ is an aralkoxycarbonyl group the cleavage can be carried out using hydrogen in the presence of a noble-metal catalyst, e.g., palladium/charcoal, in an organic solvent which is inert under the conditions of the reaction, e.g., an alkanol such as ethanol etc or an alkanecarboxylic acid ester such as ethyl acetate, and conveniently at about room temperature.

The compounds of formula IV which are used as starting materials in embodiment (c) of the process are novel and form a further object of the present invention. They can be prepared by cleaving off the alkoxycarbonyl or aralkoxycarbonyl group from a compound of the invention in which $R^1$ is a group of formula (i) and $R^8$ is an alkoxycarbonyl or aralkoxycarbonyl group. The cleavage can be carried out according to methods known per se. For example, when $R^8$ is an alkoxycarbonyl group the cleavage can be carried out using a strong inorganic acid such as a hydrohalic acid or a strong organic acid, e.g., trifluoroacetic acid, conveniently at about 0° C. to about room temperature and when $R^8$ is an aralkoxycarbonyl group the cleavage can be carried out using hydrogen in the presence of a noble-metal catalyst, e.g., palladium/charcoal, in an organic solvent which is inert under the conditions of the reaction, e.g., an alkanol such as ethanol etc or an alkanecarboxylic acid ester such as ethyl acetate, and conveniently at about room temperature.

As mentioned earlier, the compounds of the invention and pharmaceutically acceptable acid addition salts of those compounds which are basic inhibit aspartyl proteases of viral origin and are useful in the treatment and prophylaxis of viral infections, particularly of infections caused by HIV and other retroid viruses.

The in vitro inhibition of HIV protease by the compounds provided by the present invention can be demonstrated by means of the following test:

HIV protease was expressed in *E. coli* and partially purified from soluble extracts of the bacterium by ammonium sulphate fractionation (0–30%). Protease activity was assayed using the protected heptapeptide succinyl-Val-Ser-Gln-Asn-Phe-Pro-Ile isobutylamide as the substrate. Cleavage of the substrate was quantified by measuring the production of H-Pro-Ile isobutyl-amide by the spectrophotometric assay of N-terminal proline, 1.25 mM of substrate were dissolved in 125 mM of citrate buffer (pH5.5) containing 0.125 mg/ml of Tween 20. 10 ml of a solution of various concentrations of the test compound (dissolved in methanol or dimethyl sulphoxide and diluted with water containing 0.1% Tween 20) and 10 ml of protease were added to 80 ml of the above buffered substrate. Digestion was carried out at 37° C. for a fixed period of time and was terminated by the addition of 1 ml of colour reagent [30 mg/ml of isatin and 1.5 mg/ml of 2-(4-chlorobenzoyl-)benzoic acid in 10% acetone in ethanol (vol./vol.)]. The solution was heated in a water bath and then the pigmented residues were re-dissolved in 1 ml of 1% pyrogallol in 33% water in acetone (wt./vol./vol.), The optical density of the solution was measured spectrophotometrically at 599 nm, The formation of H-Pro-Ile isobutylamide in the presence of the test compound was compared with controls and the concentration of test compound required to give 50% inhibition ($I_{50}$) was determined by means of a graph plotted from the various concentrations of test compound used.

The in vitro antiviral activity of the compounds of the invention can be demonstrated in the assay described below:

This assay uses HTLV-III (strain RF) grown in C8166 cells (a human $CD4^+$ T lymphoblastoid line) using RPM1 1640 medium with bicarbonate buffer, antibiotics and 10% foetal bovine serum.

A suspension of cells is infected with ten times the $TCID_{50}$ of virus and adsorption is allowed to proceed for 90 minutes at 37° C. The cells are washed three times with medium. The test is carried out in 6 ml tissue culture tubes containing $2 \times 10^5$ infected cells in 1.5 ml of medium. Test compounds are dissolved in either aqueous medium or dimethyl sulphoxide, according to solubility, and a 15 ml solution of the test compound is added. The cultures are incubated at 37° C. for 72 hours in a humidified atmosphere containing 5% carbon dioxide in air. The cultures are then centrifuged and an aliquot of the supernatant is solubilized with Nonidet P40 and subjected to an antigen capture assay which uses a primary antiserum with particular reactivity against the viral p24 antigen and a horseradish peroxidase detection system. Colour generation is measured spectrophotometrically and is plotted against the concentration of test compound. The concentration which produces 50% protection is determined ($I_{50}$).

The results obtained in the foregoing tests using representative compounds of the invention are compiled in the following Table:

TABLE

| Compound | HIV protease inhibition $I_{50}$ (nmol) | Activity against HIV $I_{50}$ (nmol) |
| --- | --- | --- |
| A | 2 | 46 |
| B | 57 | 1000 |
| C | 1.4 | 4 |
| D | 1.3 | NT |
| E | 1.9 | NT |
| F | 2.0 | NT |

NT = not tested.

Compound A=2(S)-[3(S)-[[N-(benzyloxycarbonyl)-L-asparaginyl]amino]-2(R)-hydroxy-4-phenylbutyl]-N-tert.butyl-1(R)-cyclohexanecarboxamide.
Compound B=2(R)-[3(S)-[[N-(benzyloxycarbonyl)-L-asparaginyl]amino]-2(R)-hydroxy-4-phenylbutyl]-N-tert.butyl-1(R)-cyclohexanecarboxamide.
Compound C=2(S)-[3(S)-[[N-(2-quinolylcarbonyl)-L-asparaginyl]amino]-2(R)-hydroxy-4-phenylbutyl]-N-tert.butyl-1(R)-cyclohexanecarboxamide.
Compound D=2(S)-[3(S)-[[N-(benzyloxycaxbonyl)-S-methyl-L-cysteinyl]amino]-2(R)-hydroxy-4-phenylbutyl]-N-tert.butyl-1(R)-cyclohexanecarboxamide.
Compound E=2(S)-[3(S)-[[N-(benzyloxycarbonyl)-O-methyl-L-aspartyl]amino]-2(R)-hydroxy-4-phenylbutyl]-N-tert.butyl-1(R)-cyclohexanecarboxamide.
Compound F=2(S)-[3(S)-[[N-(benzyloxycarbonyl)-3-cyano-L-alanyl]amino]-2(R)-hydroxy-4-phenylbutyl]-N-tert.butyl-1(R)-cyclohexanecarboxamide.

The compounds of the invention and the pharmaceutically acceptable salts of those compounds of the invention which are basic can be used as medicaments, for example in the form of pharmaceutical preparations. The pharmaceutical preparations can be administered enterally such as orally, e.g., in the form of tablets, coated tablets, dragees, hard and soft gelatine capsules, solutions, emulsions or suspensions, nasally, e.g., in the form of nasal sprays, rectally, e.g., in the form of suppositories, or parenterally such as intramuscularly or intravenously, e.g., in the form of injection solutions.

For the manufacture of pharmaceutical preparations the aforementioned compounds and salts can be processed with therapeutically inert, inorganic or organic excipients. Lactose, maize starch or derivatives thereof, talc, stearic acid or its salts can be used, for example, as such excipients for tablets, coated tablets, dragees and hard gelatine capsules. Suitable excipients for soft gelatine capsules are, for example, vegetable oils, waxes, fats, semi-solid and liquid polyols and the like. Depending on the nature of the active ingredient no excipients are, however, generally required in the case of soft gelatine capsules. Suitable excipients for the manufacture of solutions and syrups are, for example, water, polyols, saccharose, invert sugar, glucose and the like. Suitable excipients for the manufacture of injection solutions are, for example, water, alcohols, polyols, glycerine, vegetable oils and the like. Natural and hardened oils, waxes, fats, semi-liquid polyols and the like are suitable excipients for the manufacture of suppositories.

The pharmaceutical preparations can also contain preservatives, stabilizers, wetting agents, emulsifiers, sweeteners, colorants, flavorants, salts for adjustment of the osmotic pressure, buffers, coating agents or antioxidants. They can also contain other therapeutically active substances.

Medicaments containing a compound-of the invention or a pharmaceutically acceptable salt of a basic compound of the invention and a therapeutically inert excipient as well as a process for the manufacture of such medicaments are also objects of the present invention. This process comprises bringing a compound of the invention or an aforementioned salt thereof into a galenical administration form together with a therapeutically inert excipient and, if desired, one or more other therapeutically active substances.

As mentioned earlier, the compounds of the invention and their aforementioned salts can be used in the control or prevention of illnesses, especially in the prophylaxis or treatment of viral infections, particularly of retroviral infections. The dosage can vary within wide limits and will, of course, be adjusted to the individual requirements in each particular case. In general, in the case of oral administration a daily dosage of about 3 mg to about 3 g, preferably about 10 mg to about 1 g, should be appropriate, although the upper limit may be exceeded when this is found to be expedient. The daily dosage can be administered as a single dosage or in divided dosages.

The following Examples illustrate the present invention:

EXAMPLE 1

A solution of 100 mg (0.20 mmol) of 2(S)-[[4(S)-benzyl-3-(tert.butoxycarbonyl)-2,2-dimethyl-5(R)-oxazolidinyl] methyl]-N-tert.butyl-1(R)-cyclohexanecarboxamide and 3.3 mg (0.017 mmol) of p-toluenesulphonic acid in 3 ml of methanol was kept at room temperature for 40 hours. The solvent was removed by evaporation and the residue was partitioned between 10 ml of dichloromethane and 2 ml of saturated sodium hydrogen carbonate solution. The organic solution was dried over anhydrous magnesium sulphate and evaporated to give 90 mg of a gum. The crude product was chromatographed on a column of silica gel using 33% ethyl acetate/hexane for the elution to give 45 mg of 2(S)-[3(S)-(tert.butoxyformamido)-2(R)-hydroxy-4-phenylbutyl]-N-tert.butyl-1(R)-cyclohexanecarboxamide; MS m/e 447 [M+H]$^+$.

The 2(S)-[[4(S)-benzyl-3-(tert.butoxycarbonyl)-2,2-dimethyl-5(R)-oxazolidinyl]methyl]-N-tert.butyl-1(R)-cyclohexanecarboxamide used as the starting material was prepared as follows:

(i) A solution of 4.375 g (31 mmol) of trans-4-cyclohexene-1(R),2(R)-dimethanol and 4.66 g (31 mmol) of tert.butyldimethylsilyl chloride in 16 ml of dimethylformamide was stirred under nitrogen and cooled to 0° C. 5.30 g of imidazole were added and the mixture was allowed to warm to room temperature and was then stirred overnight 200 ml of water were added and the mixture was extracted with three 100 ml portions of diethyl ether. The combined extracts were washed with 100 ml of water, dried over anhydrous magnesium sulphate and evaporated to give 6.50 g of an oil. This was chromatographed on a column of silica gel using 10% ethyl acetate in hexane for the elution to give 2.80 g of trans-1(R),2(R)-bis-[[(tert.butyl)(dimethyl)silyloxy]methyl]-4-cyclohexene as a colourless oil. Further elution of the column gave 2.576 g of trans-6(R)-[[(tert.-butyl)(dimethyl)silyloxy]methyl]-3-cyclohexene-1(R)-methanol as a colourless oil; MS m/e 257 [M+H]$^+$.

(ii) A solution of 2.57 g (10 mmol) of the second product from paragraph (i) in 50 ml of ethanol was hydrogenated over 130 mg of 10% palladium/carbon catalyst at room temperature and atmospheric pressure for 1 hour. The catalyst was removed by filtration and the filtrate was evaporated to give 2.30 g of trans-2(R)-[[(tert.butyl)(dimethyl)silyloxy]methyl]-1(R)-cyclohexanemethanol as a colourless oil; MS m/e 259 [M+H]$^+$.

(iii) A solution of 1.17 g (9.2 mmol) of oxalyl chloride in 23 ml of dichloromethane was stirred under nitrogen and cooled to −78° C. A solution of 1.3 ml (1.43 g, 18 mmol) of anhydrous dimethyl sulphoxide in 5 ml of dichloromethane was added over a period of 6 minutes. The mixture was stirred for a further 2 minutes and then a solution of 2.30 g (8.9 mmol) of the product from paragraph (ii) in 10 ml of dichloromethane was added over a period of 9 minutes. The mixture was stirred at −70° C. for 20 minutes and then 5.5 ml (3.99 g, 39 mmol) of triethylamine were added over a period of 6 minutes. The mixture was then allowed to warm to room temperature and 40 ml of water were added. The phases were separated and the aqueous solution was extracted with two 50 ml portions of dichloromethane. The combined organic solutions were dried over anhydrous magnesium sulphate and evaporated to give 2.45 g of a colourless oil. This was purified by chromatography on a column of silica gel using 2.5% ethyl acetate in hexane for the elution to give 1.53 g of trans-2(R)-[[(tert.butyl)(dimethyl)silyloxy]methyl]-1(R)-cyclohexanecarboxaldehyde as a colourless gum; MS m/e 257 [M+H]$^+$.

(iv) 3.46 ml (8.6 mmol) of a 2.5M solution of n-butyllithium in hexane were added over 5 minutes to a stirred suspension of 3.08 g (8.6 mmol) of methyl triphenylphosphonium bromide in 23 ml of diethyl ether. The mixture was stirred at room temperature for 85 minutes and then a solution of 1.53 g (6.0 mmol) of the product from paragraph (iii) in 10 ml of diethyl ether was added over a period of 5 minutes. The mixture was stirred at room temperature for 140 minutes, 20 ml of water were added and the phases were separated. The aqueous solution was extracted with two 20 ml portions of diethyl ether and the combined organic solutions were washed with 20 ml of water, dried over anhydrous magnesium sulphate and evaporated to give 1.85 g of an oil. This was purified by chromatography on a column of silica gel using 1% ethyl acetate in hexane for the elution to give 0.870 g of trans-1(R)-[[(tert.butyl)(dimethyl)-silyloxy]methyl]-2(S)-vinylcyclohexane as a colourless oil; MS m/e 239 [M—CH$_3$]$^+$.

(v) A solution of 870 mg (3.4 mmol) of the product from paragraph (iv) in 6 ml of a 1M solution of tetrabutylammonium fluoride in tetrahydrofuran was kept at room temperature for 3.5 hours. The solvent was then evaporated and the residue was taken up in 30 ml of water and extracted with three 20 ml portions of diethyl ether. The combined extracts were dried over anhydrous magnesium sulphate and evaporated to give 910 mg of a colourless oil. This was chromatographed on a column of silica gel using 20% ethyl acetate in hexane for the elution to give 435 mg of trans-2(S)-vinyl-1(R)-cyclohexanemethanol as a colourless-oil; MS m/e 141 [M+H]$^+$.

(vi) A solution of 435 mg (3.1 mmol) of the product from paragraph-(v) in 10 ml of pyridine was stirred under nitrogen and cooled in an ice-bath. 265 ml (391 mg; 3.4 mmol) of methanesulphonyl chloride were added, the ice-bath was removed and the mixture was stirred at room temperature for 4 hours. The solvent was removed by evaporation and the residue was partitioned between 30 ml of 2M hydrochloric acid and 30 ml of diethyl ether. The aqueous solution was extracted with two 30 ml portions of diethyl ether and the combined extracts were washed with 30 ml of 2M hydrochloric acid, 30 ml of saturated sodium hydrogen carbonate solution and 30 ml of water, dried over anhydrous magnesium sulphate and evaporated to give 615 mg of 1(R)-[(methanesulphonyloxy)methyl]-2(S)-vinylcyclohexane as a colourless oil; MS m/e 219 [M+H]$^+$.

(vii) A mixture of 1.55 g (7.1 mmol) of the product from paragraph (vi) and 935 mg (10.7 mmol) of lithium bromide in 20 ml of dimethylformamide was stirred at 60° C. under nitrogen for 50 hours. The mixture was then poured into 250 ml of water and extracted with three 100 ml portions of diethyl ether. The combined extracts were washed with 200 ml of water, dried over anhydrous magnesium sulphate and evaporated to give 1.312 g of trans-1(R)-bromomethyl-2(S)-vinylcyclohexane as a colourless liquid; MS m/e 123 [M—Br]$^+$.

(viii) A mixture of 172 mg (7.1 mmol) of magnesium turnings and a crystal of iodine in 2 ml of tetrahydrofuran was stirred under argon and 1.113 g (5.5 mmol) of the product from paragraph (vii) was added over a period of 3 minutes. The mixture was stirred and refluxed for 1 hour and then cooled to room temperature. A solution of 683 mg (2.74 mmol) of tert.-butyl (L-α-formylphenethyl) carbamate in 5 ml of tetrahydro-furan was added over a period of 10 minutes and the mixture was stirred for a further 2.5 hours at room temperature. 30 ml of 10% ammonium chloride solution were then added, the mixture was adjusted to pH 2 with 2M hydrochloric acid and then extracted with three 25 ml portions of ethyl acetate. The combined extracts were washed with 25 ml of saturated sodium hydrogen carbonate solution and 25 ml of water, dried over anhydrous magnesium sulphate and evaporated to give 1.19 g of an oil. This was chromatographed on a column of silica gel using 20% ethyl acetate/hexane for the elution to give 630 mg of a mixture of 1(S)-[3(S)-(tert.butoxyformamido)-2(S)-hydroxy-4-phenylbutyl]-2(S)-vinylcyclohexane and 1(S)-[3(S)-(tert.butoxyformamido)-2(R)-hydroxy-4-phenylbutyl]-2(S)-vinylcyclohexane as a white crystalline solid; MS m/e 374 [M+H]$^+$. The diastereomeric mixture was used in the next step without further purification.

(ix) A solution of 630 mg (1.7 mmol) of the product from paragraph (viii) in 20 ml of dimethylformamide was stirred and cooled to 0° C. 4.48 g (12 mmol) of pyridinium dichromate were added and the mixture was stirred at 0° C. for 10 minutes. The cooling bath was then removed and the mixture was stirred at room temperature for 6 hours and then poured into 170 ml of water. The resulting mixture was extracted with three 80 ml portions of ethyl acetate and the combined extracts were washed with 100 ml of water, dried over anhydrous magnesium sulphate and evaporated to give 640 mg of 1(S)-[3(S)-(tert.butoxyformamido)-2-oxo-4-phenylbutyl]-2(S)-vinylcyclohexane as a colourless oil which crystallized on standing. This product was used in the next step without further purification.

(x) A solution of 640 mg (1.7 mmol) of the product from paragraph (ix) in 35 ml of ethanol was stirred at 0° C. and 368 mg (9.7 mmol) of sodium borohydride were added. The mixture was stirred at 0° C. for 2.5 hours and the solvent was then removed by evaporation. The residue was partitioned between 100 ml of water and 100 ml of ethyl acetate, the phases were separated, and the aqueous phase was extracted with separate 100 ml and 50 ml portions of ethyl acetate. The combined extracts were dried over anhydrous magnesium sulphate and evaporated to give 595 mg of a white oily solid. This was chromatographed on a column of silica gel using 20% ethyl acetate/hexane for the elution to give 85mg of 1(S)-[3(S)-(tert.butoxyformamido)-2(S)-hydroxy-4-phenylbutyl]-2(S)-vinylcyclohexane as a white waxy solid; MS m/e 374 [M+H]$^+$. Further elution of the column yielded 263 mg of 1(S)-[3(S)-(tert.butoxyformamido)-2(R)-hydroxy-4-phenylbutyl]-2(S)-vinylcyclohexane as a white solid; MS m/e 374 [M+H]$^+$.

(xi) A solution of 370 mg (0.99 mmol) of the second product from paragraph (x) and 225 mg (1.2 mmol) of p-toluenesulphonic acid monohydrate in 7 ml of 2,2-dimethoxypropane was kept at room temperature overnight. The solution was diluted with 45 ml of diethyl ether and washed with two 40 ml portions of sodium hydrogen carbonate, dried over anhydrous magnesium sulphate and evaporated to give 530 mg of a yellow oil. This was chromatographed on a column of silica gel using 5% ethyl acetate/hexane for the elution to give 230 mg of 1(S)-[[4(S)-benzyl-3-(tert.butoxycarbonyl)-2,2-dimethyl-5(R)-oxazolidinyl]methyl]-2(S)-vinylcyclohexane as a pale yellow oil; MS m/e 414 [M+H]$^+$.

(xii) A solution of 670 mg (4.2 mmol) of potassium permanganate in 7 ml of water was added to a mixture of 230 mg (0.56 mmol) of the product from paragraph (xi), 123 mg of Aliquat 336, and 0.65 ml of glacial acetic acid in 8 ml of benzene. The mixture was stirred vigorously at room temperature overnight and then 428 mg of sodium metabisulphite were added. 24 ml of diethyl ether and 2.5 ml of 2M citric acid were added and the mixture was stirred for 10 minutes and then filtered. The phases were separated and the aqueous phase was extracted with two 10 ml portions of diethyl ether. The combined extracts were washed twice with 10 ml of water each time and then dried over anhydrous magnesium sulphate and evaporated to give 340 mg of an oil. This was chromatographed on a column of silica gel using 5% methanol/dichloromethane for the elution to give 210 mg of 2(S)-[[4(S)-benzyl-3-(tert.butoxycarbonyl)-2,2-dimethyl-5(R)-oxazolidinyl]methyl]-1(R)-cyclohexanecarboxylic acid as a colourless gum which was used in the next step without further purification.

(xiii) A mixture of 210 mg (0.49 mmol) of the product from paragraph (xii), 67 mg (0.49 mmol) of 1-hydroxybenzotriazole hydrate, 101 mg (0.49 mmol) of dicyclohexylcarbodiimide and 52 ml (36 mg, 0.49 mmol) of tert.butylamine in 2 ml of dimethyllformamide was stirred at room temperature under nitrogen for 20 hours. The mixture was filtered and the solid was washed with 2 ml of ethyl acetate. The combined filtrates were evaporated and the residue was partitioned between 10 ml of ethyl acetate and 10 ml of saturated sodium hydrogen carbonate solution. The phases were separated and the aqueous phase was extracted with two 10 ml portions of ethyl acetate. The combined extracts were washed with 10 ml of saturated sodium chloride solution, dried over anhydrous magnesium sulphate and evaporated to give 280 mg of an oily solid. This was extracted with two 1 ml portions of diethyl ether and discarded. The ether solutions were evaporated to yield 260 mg of crude product. This was chromatographed on a column of silica gel using 22% ethyl acetate/hexane for the elution to give 109 mg of 2(S)-[[4(S)-benzyl-3-(tert.butoxycarbonyl)-2,2-dimethyl-5(R)-oxazolidinyl]methyl]-N-tert.butyl-1(R)-cyclohexanecarboxamide as a white solid; MS m/e 487 [M+H]$^+$.

EXAMPLE 2

A mixture of 35 mg (0.1 mmol) of 2(S)-[3(S)-amino-2(R)-hydroxy-4-phenylbutyl]-N-tert-butyl-1(R)-cyclohexanecarboxamide and 44 mg (0.1 mmol) of N-benzyloxycarbonyl-L-asparagine pentafluorophenyl ester in 1 ml of dioxan was stirred at room temperature under nitrogen for 16 hours. The solvent was evaporated, the residue was taken up in 10 ml of ethyl acetate and the solution was washed with two 3 ml portions of 2M hydrochloric acid, 3 ml of 2M sodium hydroxide solution and 3 ml of saturated sodium chloride solution, dried over anhydrous magnesium sulphate and evaporated. The residue was chromatographed on a column of silica gel using 6% methanol/dichloromethane for the elution to give 34 mg of a white solid. This was recrystallized from dichloromethane/hexane to give 14 mg of 2(S)-[3(S)-[[N-(benzyloxycarbonyl)-L-asparaginyl]amino]-2(R)-hydroxy-4-phenylbutyl]-N-tert.butyl-1(R)-cyclohexanecarboxamide as a white solid of melting point 195°–199° C.; MS m/e 595 [M+M]$^+$.

The 2(S)-[3(S)-amino-2(R)-hydroxy-4-phenylbutyl]-N-tert.butyl-1(R)-cyclohexanecarboxamide used as the starting material was prepared as follows:

45 mg (0.1 mmol) of 2(S)-[3(S)-(tert.butoxyformamido)-2(R)-hydroxy-4-phenylbutyl]-N-tert.butyl-1(R)-cyclohexane-carboxamide [obtained as described in the first paragraph of Example 1] were dissolved in 2 ml of ethyl acetate and the solution was cooled to 0° C. 0.2 ml of a saturated solution of hydrogen chloride in ethyl acetate was added and the mixture was allowed to stand at room temperature overnight. A further 1.0 ml of hydrogen chloride in ethyl acetate was then added and the mixture was stirred at room temperature for a further 4 hours and then evaporated to dryness. The residue was dissolved in 10 ml of dichloromethane and the solution was washed with 2 ml of saturated sodium hydrogen carbonate solution, dried over anhydrous magnesium sulphate and evaporated to give 36 mg of 2(S)-[3(S)-amino-2(R)-hydroxy-4-phenylbutyl]-N-tert.butyl-1(R)-cyclohexanecarboxamide as a colourless gum, MS m/e 346 [M]⁺, which was used without further purification.

EXAMPLE 3

Treatment of 75 mg (0.15 mmol) of 2(R)-[[4(S)-benzyl-3-tert.butoxycarbonyl)-2,2-dimethyl-5(R)-oxazolidinyl]methyl]-N-tert.butyl-1(R)-cyclohexanecarboxamide with p-toluenesulphonic acid in methanol in a manner analogous to that described in the first paragraph of Example 1 gave 20 mg of 2(R)-[3(S)-(tert.-butoxyformamido)-2(R)-hydroxy-4-phenylbutyl]-N-tert.butyl-1(R)-cyclohexanecarboxamide; MS m/e 469 [M+Na]⁺, 447 [M+H]⁺.

The 2(R)-[[4(S)-benzyl-3-tert.butoxycarbonyl)-2,2-dimethyl-5(R)-oxazolidinyl]methyl]-N-tert.butyl-1(R)-cyclohexanecarboxamide used as the starting material was prepared as follows:

(i) A solution of 18.40 g (0.10mol) of cis-4(R)-acetoxymethyl-5(S)-hydroxymethyl)cyclohexene and 16.50 g (0.11 mol) of tert.butyldimethylsilyl chloride in 45 ml of dimethylformamide was stirred and cooled to 0° C. 17.00 g (0.25 mol) of imidazole were added and the mixture was stirred at 0° C. for 1 hour, then allowed to warm to room temperature and stirred for a further 160 minutes. The mixture was then poured into 400 ml of water and extracted with two 100 ml portions of diethyl ether. The combined extracts were washed with 200 ml of water, dried over anhydrous magnesium sulphate and evaporated to give 29.69 g of a straw-coloured liquid. The crude product was chromatographed on a column of silica gel using 10% ethyl acetate/hexane for the elution to give 20.85 g of cis-4(R)-(acetoxymethyl)-5(S)-[[(tert.butyl)(dimethyl)silyloxy]methyl]-3-cyclohexene as a colourless oil; MS m/e 299 [M+H]⁺.

(ii) 32.5 ml of 2M sodium hydroxide solution were added to a solution of 26.94 g (0.090 mol) of the product from paragraph (i) in a mixture of 90 ml of ethanol and 90 ml of tetrahydrofuran. The mixture was stirred at room temperature for 80 minutes and volatile solvents were then removed by evaporation. The residue was diluted with 520 ml of water and extracted with three 150 ml portions of diethyl ether. The combined extracts were washed with 350 ml and 100 ml of water, dried over anhydrous magnesium sulphate and evaporated to give 22.77 g of cis-6(S)-[[(tert.butyl)(dimethyl)silyloxy]methyl]-3-cyclohexene-1(R)-methanol as a colourless liquid; MS m/e 257 [M+H]⁺.

(iii) In a manner analogous to that described in Example 1(ii), 22.77 g (0.089 mol) of the product from paragraph (ii) were hydrogenated to yield 19.85 g of cis-2(S)-[[(tert.butyl)-(dimethyl)silyloxy]methyl]-1(R)-cyclohexanemethanol as a colourless liquid; MS m/e 259 [M+H]⁺.

(iv) In a manner analogous to that described in Example 1(iii), Swern oxidation of 23.15 g (0.090 mol) of the product from paragraph (iii) gave 22.78 g of cis-2(S)-[[(tert.butyl)(dimethyl)silyloxy]methyl]-1(R)-cyclohexanecarboxaldehyde as a colourless oil; MS m/e 257 [M+H]⁺.

(v) In a manner analogous to that described in Example 1(iv), treatment of 17.70 g (0.069 mol) of the product from paragraph (iv) with methyl triphenylphosphonium bromide and n-butyl lithium gave 14.51 g of cis-1(S)-[[(tert.butyl)(dimethyl)silyloxy]methyl]-2(S)-vinylcyclohexane as a colourless oil; MS m/e 255 [M+H]⁺.

(vi) In a manner analogous to that described in Example 1(v), treatment of 12.47 g (0.049 mol) of the product from paragraph (v) with tetrabutylammonium fluoride gave 6.617 g of cis-2(S)-vinyl-1(S)-cyclohexanemethanol as a colourless oil; MS m/e 141 [M+H]⁺.

(vii) A solution of 6.56 g (47 mmol) of the product from paragraph (vi) in 30 ml of toluene was added over a period of 4 minutes to a stirred suspension of 22.56 g (53 mmol) of dibromotriphenylphosphorane in 120 ml of toluene. The mixture was stirred under nitrogen at room temperature for 20 hours, then filtered and the solid was washed with 200 ml of hexane. The combined filtrates were washed with two 200 ml portions of saturated sodium hydrogen carbonate solution and 200 ml of water, dried over anhydrous magnesium sulphate and evaporated to give 7.898 g of cis-1(S)-bromomethyl-2(S)-vinylcyclohexane as a colourless liquid; MS m/e 205, 203 [M+H]⁺.

(viii) In a manner analogous to that described in Example 1(viii), treatment of 7.766 g (38 mmol) of the product from paragraph (vii) with magnesium followed by reaction with tert.butyl (L-α-formylphenethyl)carbamate gave 3.196 g of 1(R)-[3(S)-(tert.butoxyformamido)-2(S)-hydroxy-4-phenylbutyl]-2(S)-vinylcyclohexane which contained 10% of the (R)-alcohol; MS m/e 374 [M+H]⁺.

(ix) In a manner analogous to that described in Example 1(ix), oxidation of 2.81 g (7.5 mmol) of the product from paragraph (viii) with pyridinium dichromate gave 1.61 g of 1(R)-[3(S)-(tert.butoxyformamido)-2-oxo-4-phenylbutyl]-2(S)-vinyl-cyclohexane as a colourless oil which crystallized on standing; MS m/e 372 [M+H]⁺.

(x) In a manner analogous to that described in Example 1(x), reduction of 1.44 g of the product from paragraph (ix) with sodium borohydride gave 1.20 g of 1(R)-[3(S)-(tert.butoxy-formamido)-2(R)-hydroxy-4-phenylbutyl]-2(S)-vinylcyclohexane as a colourless gum which crystallized on standing; MS m/e 373 [M]⁺.

(xi) In a manner analogous to that described in Example 1(xi), treatment of 1.20 g (3.2 mmol) of the product from paragraph (x) with 2,2-dimethoxypropane gave 1.25 g of 1(R)-[[4(S)-benzyl-3-(tert.butoxycarbonyl)-2,2-dimethyl-5(R)-oxazolidinyl]methyl]-2(S)-vinylcyclohexane as a pale yellow gum; MS m/e 414 [M+H]⁺.

(xii) In a manner analogous to that described in Example 1(xii), treatment of 850 mg (2.06 mmol) of the product from paragraph (xi) with potassium permanganate gave 185 mg of 2(R)-[[4(S)-benzyl-3-(tert.butoxycarbonyl)-2,2-dimethyl-5(R)-oxazolidinyl]methyl]-1(R)-cyclohexanecarboxylic acid as a colourless gum; MS m/e 432 [M+H]⁺.

(xiii) In a manner analogous to that described in Example 1(xiii), 165 mg (0.38 mmol) of the product from paragraph (xii) were coupled with tert.butylamine to give 85 mg of 2(R)-[[4(S)-benzyl-3-(tert.butoxycarbonyl)-2,2-dimethyl-5(R)-oxazolidinyl]methyl]-N-tert.butyl-1(R)-cyclohexanecarboxamide as a white solid; MS m/e 487 [M+H]⁺.

EXAMPLE 4

In a manner analogous to that described in the first paragraph of Example 2, from 2(R)-[3(S)-amino-2(R)-hydroxy-4-phenylbutyl]-N-tert.butyl-1(R)-cyclohexanecarboxamide and N-benzyloxycarbonyl-L-asparagine pentafluorophenyl ester there was obtained 2(R)-[3(S)-[[N-(benzyloxycarbonyl)-L-asparaginyl]-amino]-2(R)-hydroxy-4-phenylbutyl]-N-tert.butyl-1(R)-cyclohexanecarboxamide as a white solid of melting point 166.5°–168° C.; MS m/e 617 [M+Na]⁺ and 595 [M+H]⁺.

The 2(R)-[3(S)-amino-2(R)-hydroxy-4-phenylbutyl]-N-tert.butyl-1(R)-cyclohexanecarboxamide used as the starting material was prepared in an analogous manner to that described in the second paragraph of Example 2 from 2(R)-[3(S)-(tert.butoxyformamido)-2(R)-hydroxy-4-phenylbutyl]-N-tert.butyl-1(R)-cyclohexanecarboxamide [obtained as described in the first paragraph of Example 3] and was used without further purification.

EXAMPLE 5

A mixture of 65 mg (0.13 mmol) of 2(S)-[3(S)-[[L-asparaginyl]amino]-2(R)-hydroxy-4-phenylbutyl]-N-tert-.butyl-1(R)cyclohexanecarboxamide and 35 mg (0.13 mmol) of quinaldic acid N-hydroxysuccinimide ester in 2 ml of tetrahydrofuran was stirred at room temperature under nitrogen for 18 hours. The solvent was removed by evaporation and the residue was partitioned between 10 ml of ethyl acetate and 10 ml of 10% sodium carbonate solution. The organic layer was washed with 10 ml of water, dried over anhydrous magnesium sulphate and evaporated. The crude product was chromatographed on a column of silica gel using 7% methanol in dichloromethane for the elution to give 80 mg of 2(S)-[3(S)-[[N-(2-quinolylcarbonyl)-L-asparginyl]amino]-2(R)-hydroxy-4-phenylbutyl]-N-tert.butyl-1(R)-cyclohexanecarboxamide as a white solid; MS m/e 616 [M+H]⁺.

The 2(S)-[3(S)-[[L-asparaginyl]amino]-2(R)-hydroxy-4-phenylbutyl]-N-tert.butyl-1(R)-cyclohexanecarboxamide used as the starting material was prepared as follows:

A solution of 80 mg (0.13 mmol) of 2(S)-[3(S)-[[N-(benzyloxycarbonyl)-L-asparaginyl]amino]-2(R)-hydroxy-4-phenylbutyl]-N-tert.butyl-1(R)-cyclohexanecarboxamide [obtained as described in the first paragraph of Example 2] in 10 ml of ethanol was hydrogenated over 10 mg of 10% palladium on carbon catalyst for 4 hours. The catalyst was removed by filtration and the filtrate was evaporated. The residue was suspended in toluene and the mixture was evaporated. This procedure was repeated once to give 65 mg of 2(S)-[3(S)-[[L-asparaginyl]amino]-2(R)-hydroxy-4-phenylbutyl]-N-tert.butyl-1(R)-cyclohexanecarboxamide as a colourless foam which was used without further purification.

EXAMPLE 6

A solution of 90mg (0.26 mmol) of 2(S)-[3(S)-amino-2(R)-hydroxy-4-phenylbutyl]-N-tert.butyl-1(R)-cyclohexanecarboxamide in 4 ml of dichloromethane was added to a mixture of 65 mg (0.26 mmol) of N-benzyloxycarbonyl-cyano-L-alanine, 35 mg (0.23 mmol) of hydroxybenzotriazole hydrate and 54 mg (0.26 mmol) of dicyclohexylcarbodiimide in 2 ml of dimethylformamide. The mixture was stirred under nitrogen at room temperature for 18 hours and then filtered. The filtrate was evaporated and the residue was partitioned between 25 ml of ethyl acetate and 10 ml of saturated aqueous sodium hydrogen carbonate solution. The organic layer was dried over anhydrous magnesium sulphate and evaporated. The crude product was chromatographed on a column of silica gel using 3% methanol in dichloromethane for the elution and the product was purified further by crystallization from a mixture of 1 ml of dichloromethane and 10 ml of hexane. There were obtained 68 mg of 2(S)-[3(S)-[[N-(benzyloxycarbonyl)-3-cyano-L-alanyl]amino]-2(R)-hydroxy-4-phenylbutyl]-N-tert.butyl-1(R)-cyclohexanecarboxamide as a white solid; MS m/e 577 [M+H]⁺.

EXAMPLE 7

In a manner analogous to that described in Example 6, 73 mg (0.29mmol) of N-benzyloxycarbonyl-L-valine were coupled with 100 mg (0.29 mmol) of 2(S)-[3(S)-amino-2(R)-hydroxy-4-phenylbutyl]-N-tert.butyl-1(R)-cyclohexanecarboxamide to give 80 mg of 2(S)-[3(S)-[[N-(benzyloxycarbonyl)-L-valyl]amino]-2(R)hydroxy-4-phenylbutyl]- N-tert.butyl-1( clohexanecarboxamide as a white solid; MS m/e 580 [M+H]⁺.

EXAMPLE 8

In a manner analogous to that described in Example 6, 78 mg (0.26 mmol) of N-benzyloxycarbonyl-L-phenylalanine were coupled with 90 mg (0.26 mmol) of 2(S)-[3(S)-amino-2(R)-hydroxy-4-phenylbutyl]-N-tert.butyl-1(R)-cyclohexanecarboxamide to give 72 mg of 2(S)-[3(S)-[[N-(benzyloxycarbonyl)-L-phenylalanyl]amino]-2(R)-hydroxy-4-phenylbutyl]-N-tert.butyl-1(R)-cyclohexanecarboxamide as a while solid; MS m/e 628 [M+H]⁺.

EXAMPLE 9

In a manner analogous to that described in Example 5, 95 mg (0.16 mmol) of 2(S)-[3(S)-[[N-(benzyloxycarbonyl)-L-valyl]amino]-2(R)-hydroxy-4-phenylbutyl]-N-tert.butyl-1(R)-cyclohexanecarboxamide were hydrogenated over 10% palladium on carbon catalyst and the product was reacted with quinaldic acid N-hydroxysuccinimide ester to give 50 mg of 2(S)-[3(S)-[[N-(2-quinolylcarbonyl)-L-valyl]amino]-2(R)-hydroxy-4-phenylbutyl]-N-tert.butyl-1(R)-cyclohexanecarboxamide as a white solid; MS m/e 601 [M+H]⁺.

EXAMPLE 10

In a manner analogous to that described in Example 6, 70 mg (0.26 mmol) of N-benzyloxycarbonyl-S-methyl-L-cysteine were coupled with 90 mg (0.26 mmol) of 2(S)-[3(S)-amino-2(R)-hydroxy-4-phenylbutyl]-N-tert.butyl-1(R)-cyclohexanecarboxamide to give 30 mg of 2(S)-[3(S)-[[N-benzyloxycarbonyl)-S-methyl-L-cysteinyl]amino]-2(R)-hydroxy-4-phenylbutyl]-N-tert.butyl-1(R)-cyclohexanecarboxamide as a white solid of melting point 143°–144° C.; MS m/e 598 [M+H]⁺.

EXAMPLE 11

220 mg (0.59 mmol) of pyridinium dichromate were added to a solution of 48 mg (0.08 mmol) of 2(S)-[3(S)-[[N-(benzyloxycarbonyl)-L-valyl]amino]-2(R)-hydroxy-4-phenylbutyl]-N-tert.butyl-1(R)-cyclohexanecarboxamide in 1 ml of dimethylformamide and the mixture was stirred at room temperature for 18 hours. 10 ml of water were added and the mixture was extracted with two 10 ml portions of ethyl acetate. The combined extracts were washed with two 10 ml portions of water, dried over anhydrous magnesium sulphate and evaporated; The crude product was chromatographed on a column of silica gel using 4% methanol in dichloromethane for the elution to give 31 mg of 2(S)-[3(S)-[[N-(benzyloxycarbonyl)-L-valyl]amino]-2-oxo-4-phenylbutyl]-N-tert.butyl-1(R)-cyclohexanecarboxamide as a white solid of melting point 186°–188° C.; MS m/e 578 [M+H]⁺.

EXAMPLE 12 in a manner analogous to that described in Example 6, 72 mg (0.26 mmol) of N-benzyloxycarbonyl-L-aspartic acid β-methyl ester were coupled with 90 mg (0.26 mmol) of 2(S)-[3(S)-amino-2(R)-hydroxy-4-phenylbutyl]-N-tert.butyl-1(R)-cyclohexanecarboxamide to give 90mg of 2(S)-[3(S)-[[N-(benzyloxycarbonyl)-O-methyl-L-aspartyl]amino]-2(R)-hydroxy-4-phenylbutyl]-N-tert.butyl-1(R)-cyclohexanecarboxamide as a colourless gum; MS m/e 610 [M+H]$^+$.

EXAMPLE 13

A mixture of 60 mg (0.13 mol) of 2(S)-[3(S)-[[L-asparaginyl]amino]-2(R)-hydroxy-4-phenylbutyl]-N-tert.butyl-1(R)-cyclohexanecarboxamide, 25 mg (0.13 mmol) of 3,5-dichlorobenzoic acid, 18 mg (0.13 mmol) of hydroxybenzotriazole hydrate and 27 mg (0.13 mmol) of dicyclohexylcarbodiimide in 2 ml of dimethylformamide was stirred at room temperature under nitrogen for 20 hours. The mixture was then filtered and the solid was washed with dichloromethane. The combined filtrate and washings were evaporated to dryness and the residue was partitioned between 50 ml of ethyl acetate and 10 ml of saturated aqueous sodium hydrogen carbonate solution. The separated organic phase was dried over anhydrous magnesium sulphate and evaporated. The residue was chromatographed on silica gel using 5% methanol in dichloromethane for the elution. The product was purified further by recrystallization from a mixture of 2 ml of dichloromethane and 10 ml of n-hexane to give 37 mg of 2(S)-[3(S)-[[N-(3,5-dichlorobenzoyl)-L-asparaginyl]amino]-2(R)-hydroxy-4-phenylbutyl]-N-tert.butyl-1(R)-cyclohexanecarboxamide as a white solid of melting point 220°–226° C.

EXAMPLE 14

In a manner analogous to that described in Example 6, 68 mg (0.26 mmol) of N-benzyloxycarbonyl-3-methyl-L-valine were coupled with 90 mg (0.26 mol) of 2(S)-[3(S)-amino-2(R)-hydroxy-4-phenylbutyl]-N-tert.butyl-1(R)-cyclohexanecarboxamide to give 40 mg of 2(S)-[3(S)-[[N-(benzyloxycarbonyl)-3-methyl-L-valyl]amino]-2(R)-hydroxy-4-phenylbutyl]-N-tert.butyl-1(R)-cyclohexanearboxamidecarboxamide as a white solid of melting point 90° C. (decomposition); MS m/e 594 [M+H]$^+$.

EXAMPLE 15

A solution of 100 mg (0.23 mmol) of 2(S)-[[4(S)-benzyl-3-(tert.butoxycarbonyl)-2,2-dimethyl-5(R)-oxazolidinyl]methyl]-1(R)-cyclohexanecaxboxylic acid (obtained as described in Example 1) in 2 ml of diethyl ether was added to 5 ml of a 0.3M solution of diazomethane in diethyl ether. The mixture was left to stand at room temperature overnight and then evaporated. The residue was dissolved in 3 ml of methanol and 4 mg of toluene-4-sulphonic acid were added. The mixture was left to stand overnight at room temperature and was then evaporated to dryness. The residue was partitioned between 10 ml of dichloromethane and 3 ml of saturated aqueous sodium hydrogen carbonate solution. The organic layer was dried over anhydrous magnesium sulphate and evaporated to give 90 mg of a gum. The crude product was chromatographed on a column of silica gel using hexane/ethyl acetate (2:1, v/v) for the elution to give methyl 2(S)-[3(S)-(tert.butoxyformamido)-2(R)-hydroxy-4-phenylbutyl]-1(R)-cyclohexanecarboxylate as a white solid of melting point 127°–128° C., MS m/e 406 [M+H]$^+$.

The following Example illustrates a typical pharmaceutical preparation containing a compound of the invention or a pharmaceutically acceptable acid addition salt of a basic compound of the invention as the active ingredient:

Example A

An aqueous solution of the active ingredient is filtered sterile and mixed while warming with a sterile gelatine solution, which contains phenol as a preservative, using amounts such that 1 ml of the resulting solution contains 3 mg of active ingredient, 150 mg of gelatine, 4.7 mg of phenol and distilled water ad 1 ml. The mixture is filled into vials of 1 ml capacity under aseptic conditions.

We claim:
1. Compounds of the formula:

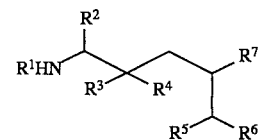

wherein R$^1$ is alkoxycarbonyl, aralkoxycarbonyl, alkanoyl, aralkanoyl, or a group of the formula:

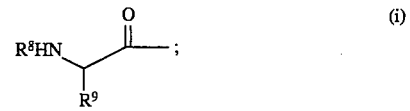

R$^2$ is alkyl, cycloalkylalkyl or aralkyl; R$^3$ is hydrogen and R$^4$ is hydroxy or R$^3$ and R$^4$ together are oxo; R$^5$ is alkoxycarbonyl or alkylcarbamoyl; R$^6$ and R$^7$ together are trimethylene or tetramethylene optionally substituted by alkyl or on adjacent carbon atoms by tetramethylene; R$^8$ is alkoxycarbonyl, aralkoxycarbonyl, alkanoyl, aroyl, or aralkanoyl; and R$^9$ is alkyl, cycloalkyl, cycloalkylalkyl, aralkyl, cyanoalkyl, carbamoylalkyl, alkylthioalkyl, alkoxyalkyl or alkoxycarbonylalkyl, and pharmaceutically acceptable acid addition salts of those compounds of formula I which are basic.

2. Compounds according to claim 1, wherein R$^1$ is a group of formula (i) in which R$^8$ is alkoxycarbonyl, aralkoxycarbonyl, alkanoyl, or aralkanoyl.

3. Compounds according to claim 1, wherein R$^1$ is alkoxycarbonyl and R$^2$ is aralkyl.

4. Compounds according to claim 3, wherein R$^1$ is tert-butoxycarbonyl, R$^2$ is benzyl, R$^3$ is hydrogen, R$^4$ is hydroxy, R$^5$ is methoxycarbonyl or tert-butylcarbamoyl, and R$^6$ and R$^7$ together are unsubstituted tetramethylene.

5. A compound in accordance with claim 4, wherein said compound is methyl 2(S)-[3(S)-(tert.butoxyformamido)-2(R)-hydroxy-4-phenylbutyl]-1(R)-cyclohexanecarboxylate.

6. A compound in accordance with claim 4, wherein said compound is 2(S)-[3(S)-(tert.butoxyformamido)-2(R)-hydroxy-4-phenylbutyl]-N-tert.butyl-1(R)-cyclohexanecarboxamide.

7. A compound in accordance with claim 4, wherein said compound is 2(R)-[3(S)-(tert.butoxyformamido)-2(R)-hydroxy-4-phenylbutyl]-N-tert.butyl-1(R)-cyclohexanecarboxamide.

8. Compounds according to claim 1, wherein R$^1$ is a group of formula (i) in which R$^8$ is aralkoxycarbonyl or aroyl and $R^9$ is alkyl, aralkyl, cyanoalkyl, carbamoylalkyl, alkylthioalkyl or alkoxycarbonylalkyl, and $R^2$ is aralkyl.

9. Compounds according to claim 8, wherein $R^3$ and $R^4$ together are oxo.

10. A compound in accordance with claim 9, wherein said compound is 2(S)-[3(S)-[[N-(benzyloxycarbonyl)-L-valyl]amino]-2-oxo-4-phenylbutyl]-N-tert.butyl-1(R)-cyclohexanecarboxamide.

11. Compounds according to claim 8, wherein $R^1$ is a group of formula (i) in which $R^8$ is benzyloxycarbonyl or 3,5-dichlorobenzoyl and $R^9$ is isopropyl, tert.butyl, benzyl, cyanomethyl, carbamoylmethyl, methylthiomethyl or methoxycarbonylmethyl, $R^2$ is benzyl, $R^3$ is hydrogen $R^4$ is hydroxy, $R^5$ is methoxycarbonyl or tert-butylcarbamoyl, and $R^6$ and $R^7$ together are unsubstituted tetramethylene.

12. A compound in accordance with claim 11, wherein said compound is 2(S)-[3(S)-[[N-(benzyloxycarbonyl)-L-asparaginyl]amino]-2(R)-hydroxy-4-phenylbutyl]-N-tert.butyl-1(R)-cyclohexanecarboxamide.

13. A compound in accordance with claim 11, wherein said compound is 2(S)-[3(S)-[[N-(benzyloxycarbonyl)-3-cyano-L-alanyl]amino]-2(R)-hydroxy-4-phenylbutyl]-N-tert.butyl-1(R)-cyclohexanecarboxamide.

14. A compound in accordance with claim 11, wherein said compound is 2(S)-[3(S)-[[N-(benzyloxycarbonyl)-L-valyl]amino]-2(R)-hydroxy-4-phenylbutyl]-N-tert.butyl-1(R)-cyclohexanecarboxamide.

15. A compound in accordance with claim 11, wherein said compound is 2(S)-[3(S)-[[N-(benzyloxycarbonyl)-L-phenylalanyl]amino]-2(R)-hydroxy-4-phenylbutyl]-N-tert.butyl-1(R)-cyclohexanecarboxamide.

16. A compound in accordance with claim 11, wherein said compound is 2(S)-[3(S)-[[N-(benzyloxycarbonyl)-S-methyl-L-cysteinyl]amino]-2(R)-hydroxy-4-phenylbutyl]-N-tert.butyl-1(R)-cyclohexane-carboxamide.

17. A compound in accordance with claim 11, wherein said compound is 2(S)-[3(S)-[[N-(benzyloxycarbonyl)-O-methyl-L-aspartyl]amino]-2(R)-hydroxy-4-phenylbutyl]-N-tert.butyl-1(R)-cyclohexane-carboxamide.

18. A compound in accordance with claim 11, wherein said compound is 2(S)-[3(S)-[[N-(3,5-dichlorobenzoyl)-L-asparaginyl]amino]-2(R)-hydroxy-4-phenylbutyl]-N-tert.butyl-1(R)-cyclohexanecarboxamide.

19. A compound in accordance with claim 11, wherein said compound is 2(S)-[3(S)-[[N-(benzyloxycarbonyl)-3-methyl-L-valyl]amino]-2(R)-hydroxy-4-phenylbutyl]-N-tert.butyl-1(R)-cyclohexane-carboxamide.

20. A compound in accordance with claim 11, wherein said compound is 2(R)-[3(S)-[[N-(benzyloxycarbonyl)-L-asparaginyl]amino]-2(R)-hydroxy-4-phenylbutyl]-N-tert.butyl-1(R)-cyclohexanecarboxamide.

* * * * *